United States Patent [19]

Angelastro et al.

[11] Patent Number: 4,891,367

[45] Date of Patent: Jan. 2, 1990

[54] 17β-(CYCLOPROPYLOXY)ANDROST-5-EN-3β-OL AND RELATED COMPOUNDS USEFUL AS $C_{17-20}$ LYASE INHIBITORS

[75] Inventors: Michael R. Angelastro, Loveland; Thomas R. Blohm, Cincinnati, both of Ohio

[73] Assignee: Merrell Dow Pharmaceuticals Inc., Cincinnati, Ohio

[21] Appl. No.: 41,170

[22] Filed: Apr. 22, 1987

[51] Int. Cl.⁴ .......................... C07J 31/00; C07J 1/00; A61K 31/565

[52] U.S. Cl. .................... 514/178; 260/397.1; 260/397.3; 260/397.4; 260/397.5; 514/177; 514/182

[58] Field of Search ............ 514/177, 178, 182; 260/397.1, 397.3, 397.4, 397.5

[56] References Cited

U.S. PATENT DOCUMENTS

| | | | |
|---|---|---|---|
| 3,135,744 | 6/1964 | Ercoli et al. | 260/239.55 |
| 3,242,198 | 3/1966 | Ercoli et al. | 260/397.4 |
| 3,475,464 | 10/1969 | Halpern | 260/397.4 |
| 3,732,209 | 5/1973 | Fahrenholtz et al. | 260/239.5 |
| 3,763,146 | 10/1973 | Edwards | 540/119 |
| 4,139,617 | 2/1979 | Grunwell et al. | 260/397.2 |
| 4,361,559 | 11/1982 | Varma | 424/243 |
| 4,420,428 | 12/1983 | Varma | 260/397 |
| 4,427,592 | 1/1984 | Varma | 260/397 |
| 4,529,548 | 6/1985 | Varma | 260/397 |

OTHER PUBLICATIONS

A. Ercoli et al., *Chemistry and Industry*, 1962, 1284.
G. Falconi, *Hormonal Steroids*, Proc. Intern. Cong. Hormonal Steroids, 1st, 1964(2), 143 (1965).
R. Gardi et al., *Steroids*, 19, 639 (1972).
Derwent Abstract 73-73280U Netherlands Patent 73-6463.

*Primary Examiner*—Mark L. Berch
*Attorney, Agent, or Firm*—John J. Kolano

[57] ABSTRACT

This invention is directed to 17β-(cyclopropyloxy)androst-5-en-3β-ol and related compounds and also to a method for using such compounds in the treatment of androgen-dependent disorders. The ethers are prepared by using the Simmons-Smith reaction and an appropriate vinyl ether.

6 Claims, No Drawings

17β-(CYCLOPROPYLOXY)ANDROST-5-EN-3β-OL AND RELATED COMPOUNDS USEFUL AS C17-20 LYASE INHIBITORS

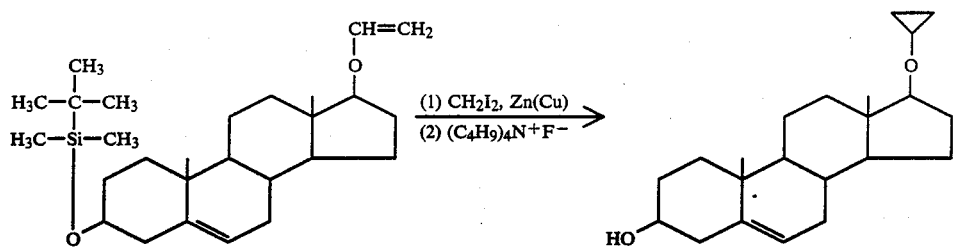

The present invention is directed to 17β-(cyclopropyloxy)androst-5-en-3β-ol and related compounds and also to a method for using such compounds in the treatment of androgen-dependent disorders. More particularly, the present invention is directed to a group of compounds having the following general formula:

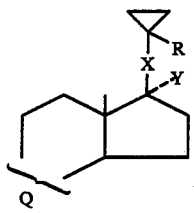

I wherein R is hydrogen or methyl; X is O or S; Y is hydrogen or $C_1$–$C_4$ alkyl; and Q is

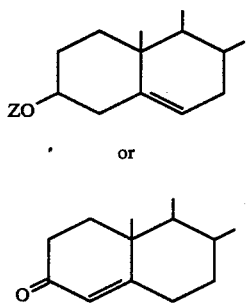

II or wherein Z is hydrogen or alkanoyl of 1–10 carbon atoms or cyclopentane- and benzene-alkanoyl wherein the alkanoyl portion contains up to 4 carbon atoms. Examples of alkanoyl groups are acetyl, propionyl, butanoyl and decanoyl; examples of the cyclopentane- and benzene-alkanoyl groups are cyclopentanepropionyl and benzenepropionyl. Preferred compounds are those in which Q is structure I.

To obtain the ethers of the present invention, an appropriate 17-vinyl ether of androst-5-ene-3β,17β-diol is reacted with methylene iodide and zinc-copper couple in a Simmons-Smith reaction to convert the vinyl ether group to a cyclopropyl ether group. The reaction is conveniently carried out on a compound in which the 3-hydroxy group is protected by a readily removable group. t-Butyldimethylsilyl ether is preferred for this purpose and this group can be readily removed, when desired, by treatment of the silyl ether with tetrabutylammonium fluoride. The process involved can be illustrated by the following reaction.

Actually, since the steroid starting material also contains a double bond at the 5-position, a Simmons-Smith reaction can take place at that position in addition to, or instead of, reaction at the 17-vinyl ether double bond. However, the major product obtained is the 17-cyclopropyl ether formed by reaction at the 17-vinyl ether double bond only and any 5,6-cyclopropa-steroids formed by reaction at the 5-double bond are removed during purification.

The product cyclopropyl ether, or a similar thioether, can be converted to the corresponding 3-keto-$\Delta^4$-compound by means of an Oppenauer oxidation using aluminum isopropoxide. For example, oxidation of 17β-(cyclopropyloxy)androst-5-en-3β-ol with aluminum isopropoxide gives 17β-(cyclopropyloxy)androst-4-en-3-one. In addition, the corresponding 3-esterified oxy compounds can be obtained by reaction of the 3-hydroxy-$\Delta^5$-compound with an appropriate acylating agent such as acetic anhydride.

To obtain the vinyl ether starting materials used above, an androst-5-ene-3β,17β-diol, in which the 3-hydroxy group is protected as the t-butyldimethylsilyl ether, is reacted with ethyl vinyl ether in the presence of mercuric acetate to give the desired starting material. The indicated silyl ether starting materials can be obtained by selective silylation of androst-5-ene-3β,17β-diol or the corresponding 17α-methyl compound. Alternatively, dehydroepiandrosterone can be silylated to give the corresponding 3-silyl ether and the 17-ketone can then be reduced to the corresponding alcohol or converted to the 17α-methyl-17β-hydroxy compound.

The thioethers of the present invention can be prepared by starting with the 3-benzyl ether of dehydroepiandrosterone. This 17-keto compound is reacted with Lawesson's reagent (4-methoxyphenylthionophosphine sulfide dimer) to give the corresponding 17-thioketone which is reduced with lithium aluminum hydride to give the 17β-thiol and then further reacted with cyclopropanone in methylene chloride to give the corresponding 17-[(1-hydroxycyclopropyl)thio]-compound. This is then reacted with hydrogen bromide to convert the cyclopropyl hydroxy-group to a bromide and give the corresponding 17-[(1-bromocyclopropyl)-thio]-compound and the bromide is finally removed and replaced with hydrogen by treatment with sodium methylthiolate in dimethylformamide and the benzyl group is removed by standard procedures to thus give the desired product.

The present compounds are useful as inhibitors of steroid $C_{17-20}$ lyase and thus inhibit testosterone formation. Consequently, they are useful for treating various androgen-dependent disorders. The present invention thus also encompasses a method for treating androgen-dependent disorders which comprises administering to an individual suffering from such a disorder an effective amount of a compound of the present invention. More particularly, the present compounds are useful in the treatment of prostatic carcinoma, benign prostatic hyperplasia and virilism and hirsutism (in women).

It is well established that reduction of serum testosterone levels is useful in the treatment of many cases of prostatic carcinoma. In clinical practice, this has been accomplished by orchiectomy or by diethylstilbestrol treatment but the first approach is often psychologically unacceptable while a number of side effects are associated with the second approach. Thus, an alternative approach to testosterone reduction is desirable and this can be accomplished by the administration of the present compounds. To the extent that prostatic carcinoma is androgen-dependent, the present compounds would block the source of androgens and thus serve as an appropriate treatment for this condition.

The activity of the present compounds as inhibitors of steroid $C_{17-20}$ lyase was established using microsomal preparations of the steroid $C_{17-20}$ lyase enzyme from human or laboratory animal testis; human testes used for this purpose were obtained from therapeutic orchiectomies. The enzyme was incubated with NADPH and the test compound in the concentration range $5 \times 10^{-8}$M to $3 \times 10^{-6}$M and the extent of inhibition of the enzyme was determined with time-dependency of inhibition being established by a decline in enzyme activity with the time of exposure to the test compound. Time-dependency of inhibition often implies irreversible inactivation of the enzyme and irreversibility was specifically established by inability to restore enzyme activity by dialysis under conditions which maintained activity of native enzyme. When tested according to the above procedure using human enzyme, the compounds of the present invention were found to inhibit the enzyme in a time-dependent manner and irreversibly.

In the treatment of the various androgen-dependent disorders described earlier, the compounds of the present invention may be administered orally to the patient being treated to achieve the particular effect desired. The amount of compound to be administered will vary over a wide range and can be any effective amount. Depending on the patient to be treated, and the severity of the condition being treated, the effective amount of compound administered will vary from about 0.625 to 62.5 mg/kg of body weight per day and preferably from 5 to 30 mg/kg of body weight per day. Unit dosages for oral administration may contain, for example, from 25 to 500 mg of a compound of the invention. Alternatively, the present compounds can be administered by parenteral routes or by implants.

In practicing the method of this invention, the active ingredient is preferably incorporated in a composition containing a pharmaceutical carrier and from about 5 to about 90% by weight of the cyclopropyl steroid. The term "pharmaceutical carrier" refers to known pharmaceuticals excipients useful in formulating pharmaceutically active compounds for internal administration to animals, and which are substantially non-toxic and non-sensitizing under conditions of use. The compositions can be prepared by known techniques for the preparation of tablets or capsules and can contain suitable excipients known to be useful in the preparation of the particular type of composition desired. Suitable pharmaceutical carriers in formulation techniques are found in standard texts, such as *Remingtons Pharmaceutical Sciences*, Mack Publishing Company, Easton, Pa.

The following examples are presented to illustrate the present invention but they should not be construed as limiting it in any way.

EXAMPLE 1

To a solution of 4 g of 3β-(t-butyldimethylsilyloxy)androst-5-en-17β-ol in 50 ml of vinyl ethyl ether, there was added 0.25 g of mercuric acetate. The mixture was stirred at room temperature for 24 hours, quenched with triethylamine, and then poured into dilute aqueous potassium carbonate solution. The aqueous mixture was extracted 3 times with 100 ml-portions of diethyl ether and the combined organic extracts were washed with saturated aqueous sodium chloride solution and then dried over sodium sulfate. The solvent was then removed under reduced pressure and the residue was purified by flash chromatography using ethyl acetate/hexane, 1:4, to give 3β-(t-butyldimethylsilyloxy)-17β-ethenyloxyandrost-5-ene.

EXAMPLE 2

To a suspension of 0.3 g of zinc dust in 3 ml of diethyl ether was added 50 mg of cuprous chloride. The resulting mixture was refluxed for 30 minutes and then 1.06 g of diiodomethane was added. The resulting solution was refluxed for 30 minutes and 0.3 g of 3β-(t-butyldimethylsilyloxy)-17β-ethenyloxyadrost-5-ene was added. The resulting mixture was refluxed for 16 hours and then diluted with 10 ml of diethyl ether and filtered. The solid which was separated was washed with ethyl acetate (3 times, 50 ml) and the combined filtrate and washings were washed with saturated aqueous ammonium chloride and dried over magnesium sulfate. The solvent was then removed under reduced pressure to leave a residual solid which was crude 3β-(t-butyldimethylsilyloxy)-17β-(cyclopropyloxy)androst-5-ene containing some 17β-(cyclopropyloxy)cycloprop[5,6]androstane product.

The crude product obtained above was mixed with 15 ml of tetrahydrofuran and 0.6 mmol of tetrabutylammonium fluoride was added. This reaction mixture was stirred for 24 hours and poured into saturated aqueous ammonium chloride solution. The resulting mixture was extracted with ethyl acetate (3 times, 100 ml) and the combined organic extracts were dried over magnesium sulfate. The solvent was then removed under reduced pressure to leave a residual crude solid which was purified by reverse phase high-pressure liquid chromatography to give 17β-(cyclopropyloxy)androst-5-en-3β-ol. MS (m/z): 371 (M+41)+, 359 (M+29)+, 331 (M+H)+, 313 (MH-H$_2$O)+, 273 (MH-58)+, 255 (MH-58-H$_2$O)+. The compound has the following structural formula:

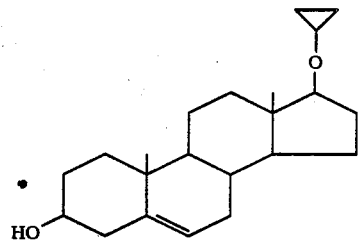

EXAMPLE 3

If the procedure of Example 1 is repeated using 2-propenyl ethyl ether instead of the vinyl ethyl ether and the resulting product is reacted with diiodomethane and zinc-copper couple as described in Example 2, the product obtained is 17β-(1-methylcyclopropyloxy)androst-5-en-3β-ol.

3β-(t-Butyldimethylsilyloxy)-17α-methylandrost-5-en-17β-ol, obtained by the reaction of 17α-methylandrost-5-en-3β,17β-diol with t-butyldimethylsilyl chloride in dimethylformamide in the presence of imidazole, is reacted with vinyl ethyl ether according to the procedure described in Example 1 and the resulting product is reacted with diiodomethane and zinc-copper couple as described in Example 2. The product obtained in this way is 17α-methyl-17β-(cyclopropyloxy)androst-5-en-3β-ol.

EXAMPLE 4

17β-(Cyclopropyloxy)androst-5-en-3β-ol is treated with acetic anhydride and pyridine. The mixture is poured into water and extracted with ethyl acetate. The ethyl acetate layer is separated and dried and the solvent is evaporated to leave as a residue, 3β-acetyloxy-17β-(cyclopropyloxy)androst-5-ene. 3β-(Cyclopentanepropionyloxy)-17β-(cyclopropyloxy)androst-5-ene and 3β-(benzenepropionyloxy)-17β-(cyclopropyloxy)androst-5-ene are obtained in a similar way using the appropriate acid chlorides.

EXAMPLE 5

3β-Benzyloxyandrost-5-en-17β-thiol is obtained starting from dehydroepiandrosterone. The dehydroepiandrosterone is reacted with one equivalent of sodium hydride and benzyl chloride by standard procedures for making benzyl ethers to give 3-benzyloxyandrost-5-en-17-one. This benzyloxy compound is then reacted with Lawesson's reagent (4-methoxyphenylthiophosphine sulfide dimer) according to the procedure described in M. Feiser, "Feiser and Feiser's Reagents for Organic Synthesis", John Wiley & Sons, New York, 1980, p. 327; also B. S. Pedersen et al., *Bull. Soc. Chim. Belg.*, 87, 223 (1978). This gives 3β-benzyloxyandrost-5-ene-17-thione and this thione is then reduced with lithium aluminum hydride by standard procedures to give the desired 17β-thiol. Then, to a solution of cyclopropanone in dichloromethane under nitrogen at −50° C., there is added rapidly 1.1 equivalent of the above thiol in dichloromethane. The temperature is allowed to rise to −30° C. and, after 16 hours, most of the solvent is evaporated. Dry ether is added to precipitate by-product polyketene. The by-product is removed by filtration, the solvent is distilled from the filtrate, and the residue is purified by flash chromatography to give 3β-benzyloxy-17β-(1-hydroxycyclopropylthio)androst-5-ene.

The above hydroxycyclopropyl compound (40 mmol) is dissolved in 50 ml of dry dichloromethane. At 0° C., hydrogen bromide gas is slowly bubbled through the solution for 30 minutes. Stirring is continued for an additional 30 minutes after which time the solution is washed with cold water, bicarbonate and water, and dried over sodium sulfate and the solvent is evaporated to leave a residual product. The treatment with hydrogen bromide replaces the hydroxy group with bromine and the product obtained is 3β-benzyloxy-17β-[(1-bromocyclopropyl)thio]androst-5-ene.

Sodium methanethiolate (0.8 mmol), 0.12 mmol of the bromocyclopropyl compound obtained above, and 0.5 mmol of di-t-butylnitroxide are dissolved in 1 ml of dry dimethylformamide at 0° C. under nitrogen. The reaction gives 3β-benzyloxy-17β-(cyclopropylthio)androst-5-ene which is then debenzylated by hydrogenation by standard procedures to give 17β-(cyclopropylthio)androst-5-en-3β-ol.

What is claimed is:

1. A compound of the formula

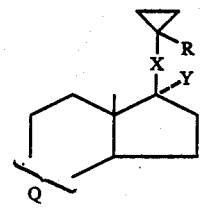

wherein R is hydrogen or methyl; X is O or S; Y is hydrogen or C₁–C₄ alkyl; and Q is

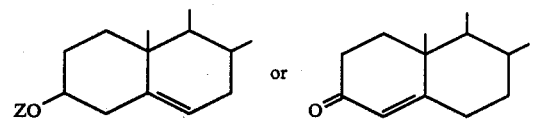

wherein Z is hydrogen or alkanoyl of 1–10 carbon atoms, or cyclopentane- and benzene-alkanoyl wherein the alkanoyl portion contains up to 4 carbon atoms.

2. A compound according to claim 1 which has the formula:

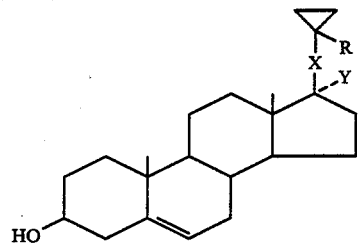

wherein R is hydrogen or methyl; X is O or S; and, Y is hydrogen or C₁–C₄ alkyl.

3. A compound according to claim 1 which is 17β-(cyclopropyloxy)androst-5-en-3β-ol.

4. A compound according to claim 1 which is 17β-(cyclopropyloxy)androst-4-en-3-one.

5. A method for treating androgen-dependent disorders which comprises administering to an individual suffering from such a disorder an effective amount of a compound of the formula

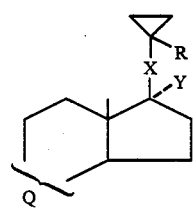

wherein R is hydrogen or methyl; X is O or S; Y is
hydrogen or C$_1$–C$_4$ alkyl; and Q is
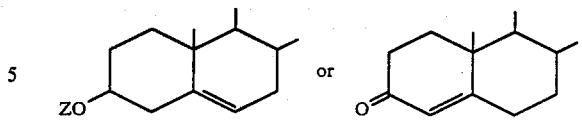 or
wherein Z is hydrogen or alkanoyl of 1–10 carbon atoms, or cyclopentane- and benzene-alkanoyl wherein the alkanoyl portion contains up to 4 carbon atoms.
6. A method according to claim 5 which comprises administering an effective amount of 17β-(cyclopropyloxy)androst-5-en-3β-ol.
* * * * *